(12) United States Patent
Boiteau et al.

(10) Patent No.: US 8,372,879 B2
(45) Date of Patent: Feb. 12, 2013

(54) 4-(HETEROCYCLOALKYL) BENZENE-1,3-DIOL COMPOUNDS AS TYROSINASE INHIBITORS, PROCESS FOR THE PREPARATION THEREOF AND USE THEREOF IN HUMAN MEDICINE AND ALSO IN COSMETICS

(75) Inventors: Jean-Guy Boiteau, Valbonne (FR); Jean-Claude Pascal, Nice (FR)

(73) Assignee: Galderma Research & Development, Biot (FR)

( * ) Notice: Subject to any disclaimer, the term of this patent is extended or adjusted under 35 U.S.C. 154(b) by 0 days.

(21) Appl. No.: 13/131,161

(22) PCT Filed: Dec. 2, 2009

(86) PCT No.: PCT/EP2009/066267
§ 371 (c)(1),
(2), (4) Date: Nov. 7, 2011

(87) PCT Pub. No.: WO2010/063773
PCT Pub. Date: Jun. 10, 2010

(65) Prior Publication Data
US 2012/0041213 A1  Feb. 16, 2012

Related U.S. Application Data

(60) Provisional application No. 61/202,128, filed on Jan. 30, 2009.

(30) Foreign Application Priority Data

Dec. 2, 2008 (FR) ..................... 08 58206

(51) Int. Cl.
*A61K 31/382* (2006.01)
*A61K 31/351* (2006.01)
*C07D 335/02* (2006.01)
*C07D 309/06* (2006.01)
*C07D 311/96* (2006.01)

(52) U.S. Cl. .......... 514/432; 514/451; 549/13; 549/427; 549/331

(58) Field of Classification Search .................. 549/13, 549/427, 331; 514/432, 451
See application file for complete search history.

(56) References Cited

FOREIGN PATENT DOCUMENTS

| WO | 9523780 A | 9/1995 |
|----|-----------|--------|
| WO | 9915148 A | 4/1999 |
| WO | 0056279 A | 9/2000 |
| WO | 0119323 A | 3/2001 |
| WO | 0220474 A | 3/2002 |
| WO | 2004052330 A | 6/2004 |

OTHER PUBLICATIONS

Vippagunta et al., Crystalline solids, 2001, Advanced Drug Delivery Reviews, 48, pp. 3 and 18.*
International Search Report dated Mar. 29, 2010 issued in International Application No. PCT/EP2009/066267.

* cited by examiner

*Primary Examiner* — Kristin Bianchi
(74) *Attorney, Agent, or Firm* — SNR Denton US LLP

(57) ABSTRACT

4-(heterocycloalkyl)benzene-1,3-diol compounds are described corresponding to general formula (I) below:

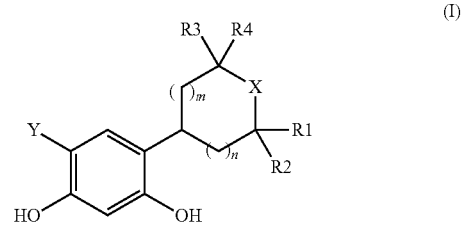

Also described, are compositions including the same, processes for preparation thereof and to the use thereof in pharmaceutical or cosmetic compositions for use in the treatment or prevention of pigmentary disorders.

7 Claims, 1 Drawing Sheet

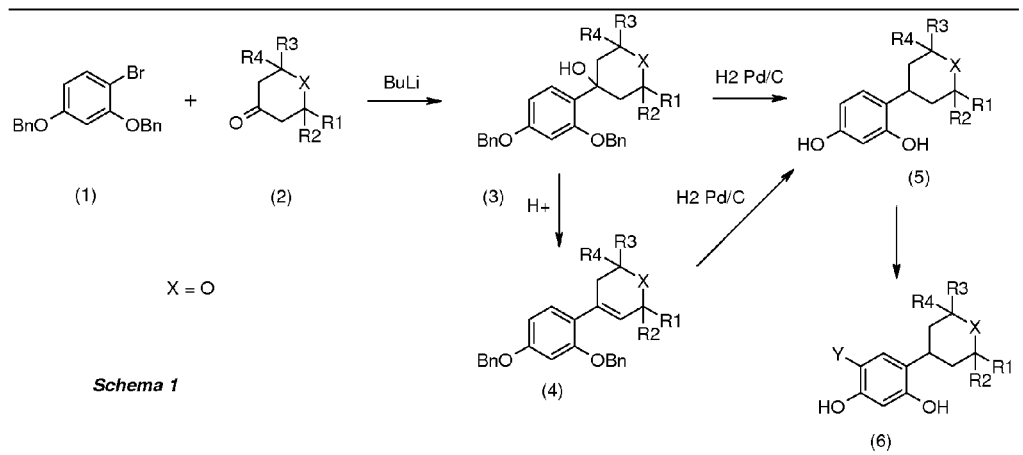
Schema 1
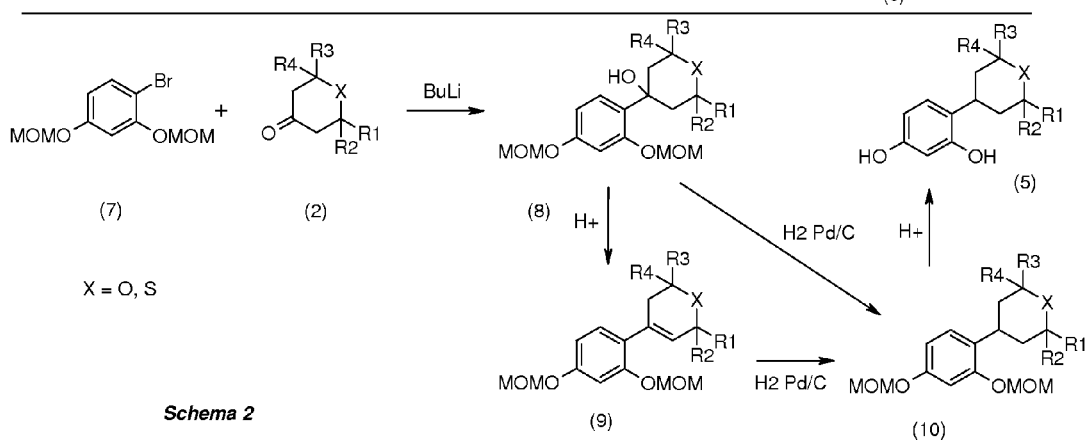
Schema 2
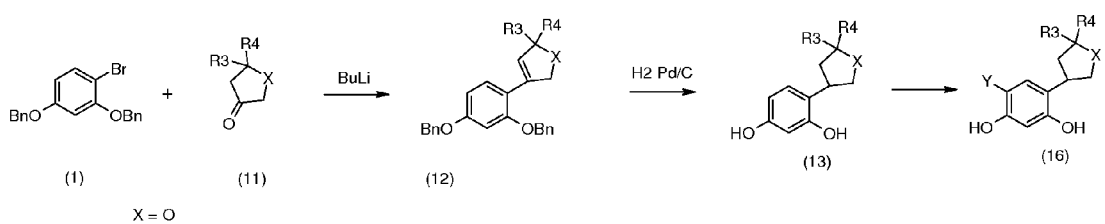
Schema 3
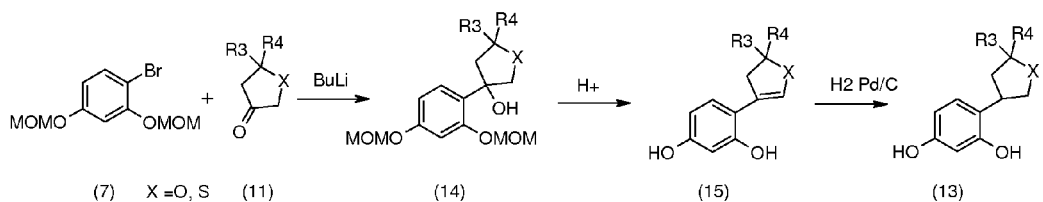
Schema 4

4-(HETEROCYCLOALKYL) BENZENE-1,3-DIOL COMPOUNDS AS TYROSINASE INHIBITORS, PROCESS FOR THE PREPARATION THEREOF AND USE THEREOF IN HUMAN MEDICINE AND ALSO IN COSMETICS

This application claims priority under 35 U.S.C. §119 of FR 0858206, filed Dec. 2, 2008, and U.S. Provisional Application Ser. No. 61/202,128, filed Jan. 30, 2009, and is the United States national phase of PCT/EP2009/066267, filed Dec. 2, 2009, and designating the United States (published in the English language on Jun. 10, 2010, as WO 2010/063773 A1; the title and abstract were also published in English), each hereby expressly incorporated by reference in its entirety and each assigned to the assignee hereof.

The invention relates to novel 4-(heterocycloalkyl)benzene-1,3-diol compounds as industrial and useful products. It also relates to the process for the preparation thereof and to the use thereof, as tyrosinase inhibitors, in pharmaceutical or cosmetic compositions for use in the treatment or prevention of pigmentary disorders.

Skin pigmentation, in particular human skin pigmentation, is the result of melanin synthesis by dendritic cells, melanocytes. Melanocytes contain organelles called melanosomes which transfer melanin into the upper layers of keratinocytes which are then transported to the surface of the skin through differentiation of the epidermis (Gilchrest B A, Park H Y, Eller M S, Yaar M, Mechanisms of ultraviolet light-induced pigmentation. Photochem Photobiol 1996; 63: 1-10; Hearing V J, Tsukamoto K, Enzymatic control of pigmentation in mammals. FASEB J 1991; 5: 2902-2909).

Among the enzymes of melanogenesis, tyrosinase is a key enzyme which catalyses the first two steps of melanin synthesis. Homozygous mutations of tyrosinase cause oculocutaneous albinism type I characterized by a complete lack of melanin synthesis (Toyofuku K, Wada I, Spritz R A, Hearing V J, The molecular basis of oculocutaneous albinism type 1 (OCA1): sorting failure and degradation of mutant tyrosinases results in a lack of pigmentation. Biochem J 2001; 355: 259-269).

In order to treat pigmentation disorders resulting from an increase in melanin production, for which there is no treatment that meets all the expectations of patients and dermatologists, it is important to develop new therapeutic approaches.

Most of the skin-lightening compounds that are already known are phenols or hydroquinone derivatives. These compounds inhibit tyrosinase, but the majority of them are cytotoxic to melanocytes owing to the formation of quinones. There is a risk of this toxic effect causing a permanent depigmentation of the skin. The obtaining of compounds that can inhibit melanogenesis while at the same time being very weakly cytotoxic or devoid of toxicity to melanocytes is most particularly sought.

Among the compounds already described in the literature, patent application WO 99/15148 discloses the use of 4-cycloalkyl resorcinols as depigmenting agents.

Patent FR2704428 discloses the use of 4-halo-resorcinols as depigmenting agents.

Patent applications WO 2006/097224 and WO 2006/097223 disclose the use of 4-cycloalkylmethyl resorcinols as depigmenting agents.

Patent application WO 2005/085169 discloses the use of alkyl 3-(2,4-dihydroxyphenyl)propionate as a depigmenting agent.

Patent application WO 2004/017936 discloses the use of 3-(2,4-dihydroxyphenyl)acrylamide as a depigmenting agent.

Patent application WO 2004/052330 discloses the use of 4-[1,3]dithian-2-yl resorcinols as depigmenting agents.

More particularly, patent EP0341664 discloses the use of 4-alkyl resorcinols as depigmenting agents, among which 4-n-butyl resorcinol, also known as rucinol, is part of the composition of a depigmenting cream sold under the name Iklen®.

The applicant has now discovered, unexpectedly and surprisingly, that novel compounds having a 4-(heterocycloalkyl)benzene-1,3-diol structure have a very good tyrosinase enzyme-inhibiting activity and a very low cytotoxicity. Furthermore, these compounds have a tyrosinase enzyme-inhibiting activity that is greater than that of rucinol, while at the same time being less cytotoxic with respect to melanocytes than rucinol.

These compounds find uses in human medicine, in particular in dermatology, and in the cosmetics field.

Thus, the present invention relates to the compounds of general formula (I) below:

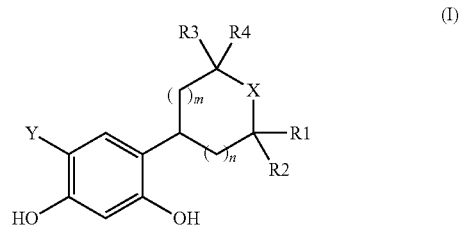

in which:
R1, R2, R3 and R4, which may be identical or different, represent:
 a hydrogen,
 a $C_1$-$C_4$ alkyl radical,
 a hydroxymethyl, a hydroxyethyl,
 a ($C_1$-$C_4$ alkoxy) carbonyl,
 a $C_1$-$C_4$ alkoxy,
 a hydroxyl,
or
R1 and R2 are linked to one another and form a carbon ring containing 5 or 6 carbon atoms, with the carbon atom to which they are attached, and R3 and R4, which may be identical or different, represent:
 a hydrogen,
 a $C_1$-$C_4$ alkyl radical,
or
R1 and R4 are linked to one another and form a —$(CH_2)_2$— or —$(CH_2)_3$— chain and R2 and R3, which may be identical or different, represent:
 a hydrogen,
 a $C_1$-$C_4$ alkyl radical,
X represents an oxygen atom or a sulphur atom.
Y represents a hydrogen, a chlorine atom or a fluorine atom.
m can have the value 1 or 2 and n can have the value 0 or 1, and when n=0, then m=1 or 2, and when n=1, then m=1,
and also the salts of the compounds of general formula (I), and the isomer and enantiomer forms thereof.

Among the salts of the compounds of general formula (I) with a pharmaceutically acceptable base, mention may preferably be made of the salts with an organic base or with an inorganic base.

The suitable inorganic bases are, for example, potassium hydroxide, sodium hydroxide or calcium hydroxide.

The suitable organic bases are, for example, morpholine, piperazine or lysine.

The compounds of general formula (I) may also exist in the form of hydrates or of solvates.

The solvents that are suitable for forming solvates are, for example, alcohols such as ethanol or isopropanol.

According to the present invention, the term "$C_1$-$C_4$ alkyl" denotes a linear or branched, saturated hydro-carbon-based chain containing from 1 to 4 carbon atoms.

According to the present invention, the term "($C_1$-$C_4$ alkoxy) carbonyl" denotes a carboxyl radical substituted with an alkyl radical containing from 1 to 4 carbon atoms.

According to the present invention, the term "$C_1$-$C_4$ alkoxy" denotes an oxygen atom substituted with a linear or branched, saturated hydrocarbon-based chain containing from 1 to 4 carbon atoms.

According to the present invention, the term "isomers" denotes the cis and trans forms relative to the substituents on the heterocycloalkyl at position 4 of the benzene-1,3-diol.

According to the present invention, the compounds of general formula (I) that are particularly preferred are those for which:
R1 represents a hydrogen, a $C_1$-$C_4$ alkyl radical or a hydroxymethyl radical,
R2 represents a hydrogen,
R3 represents a hydrogen,
R4 represents a hydrogen,
X represents an oxygen atom,
Y represents a hydrogen or a fluorine atom,
m=1 and n=1,
and also the salts of these compounds of general formula (I), and the isomer and enantiomer forms thereof.

Among the compounds of formula (I) which fall within the context of the present invention, mention may in particular be made of the following:
1: 4-(tetrahydropyran-4-yl)benzene-1,3-diol
2: 4-(tetrahydrothiopyran-4-yl)benzene-1,3-diol
3: 4-(cis-2,6-dimethyltetrahydropyran-4-yl)benzene-1,3-diol
4: trans-4-(2-methyltetrahydropyran-4-yl)benzene-1,3-diol
5: cis-4-(2-methyltetrahydropyran-4-yl)benzene-1,3-diol
6: trans-4-(2-ethyltetrahydropyran-4-yl)benzene-1,3-diol
7: cis-4-(2-ethyltetrahydropyran-4-yl)benzene-1,3-diol
8: trans-4-(2-hydroxymethyltetrahydropyran-4-yl)-benzene-1,3-diol
9: 4-(2,2,6,6-tetramethyltetrahydropyran-4-yl)benzene-1,3-diol
10: 4-(tetrahydrofuran-3-yl)benzene-1,3-diol
11: 4-(tetrahydrothiophen-3-yl)benzene-1,3-diol
12: 4-(6-oxaspiro[4.5]dec-9-yl)benzene-1,3-diol
13: 4-chloro-6-(tetrahydropyran-4-yl)benzene-1,3-diol
14: 4-fluoro-6-(tetrahydropyran-4-yl)benzene-1,3-diol
15: 4-(2,2-diethyltetrahydropyran-4-yl)benzene-1,3-diol
16: 4-(tetrahydropyran-3-yl)benzene-1,3-diol
17: trans-4-(5-hydroxymethyltetrahydrofuran-3-yl)-benzene-1,3-diol
18: cis-4-(5-hydroxymethyltetrahydrofuran-3-yl)benzene-1,3-diol
19: trans-4-fluoro-6-(5-hydroxymethyltetrahydrofuran-3-yl)benzene-1,3-diol
20: cis-4-fluoro-6-(5-hydroxymethyltetrahydrofuran-3-yl)benzene-1,3-diol
21: trans-4-fluoro-6-(2-hydroxymethyltetrahydropyran-4-yl)benzene-1,3-diol
22: cis-4-fluoro-6-(2-hydroxymethyltetrahydropyran-4-yl)benzene-1,3-diol
23: cis-4-(8-oxabicyclo[3.2.1]oct-3-yl)benzene-1,3-diol
24: trans-4-(8-oxabicyclo[3.2.1]oct-3-yl)benzene-1,3-diol
25: 4-fluoro-6-(tetrahydrothiopyran-4-yl)benzene-1,3-diol The compounds of general formula (I) are prepared according to the general reaction schemes 1 to 4 shown in FIG. 1.

Scheme 1 of FIG. 1 corresponds to the preparation of the compounds of general formula (I) for which m=n=1, X═O and R1, R2, R3, R4 and Y have the same definition as above.

According to this reaction scheme 1 of FIG. 1, the 2,4-dibenzyloxybromobenzene (1) is reacted, in the presence of butyllithium, with a heterocycloalkanone of general formula (2), which is commercially available or prepared according to conventional synthesis methods (W. D. Langley, Org. Synth. I, 122 (1932)) so as to give the benzyl alcohol of general formula (3).

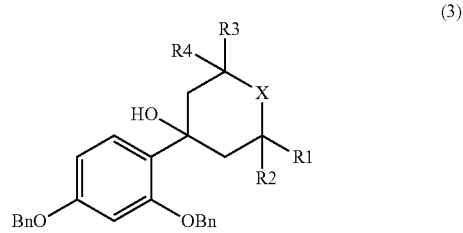

(3)

The benzyl alcohol of general formula (3) is dehydrated in an aprotic solvent such as toluene, in the presence of an acid such as camphorsulphonic acid, for example, so as to give a compound of general formula (4).

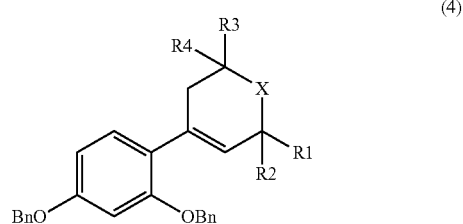

(4)

The compounds of general formula (5):

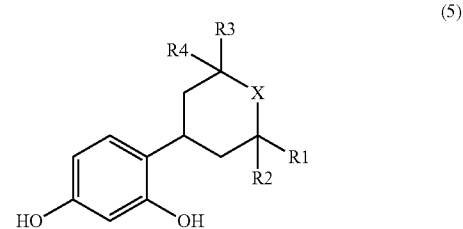

(5)

are obtained either starting from the compounds of general formula (3), or starting from the compounds of general formula (4), by hydrogenation in a solvent such as methanol, for example, and in the presence of hydrogen and of a palladium-based catalyst such as palladium-on-charcoal, for example.

The compounds of general formula (6):

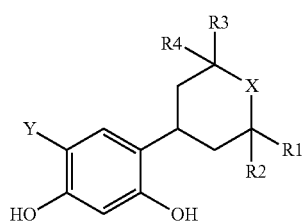
(6)

are obtained by halogenation of the compounds of general formula (5) using a halogenating agent such as N-chlorosuccinimide (Y=Cl), or Selectfluor® (Y=F), for example.

Scheme 2 of FIG. 1 corresponds to the preparation of the compounds of general formula (I) for which m=n=1, X=O or S, and R1, R2, R3, R4 and Y have the same definition as above.

According to reaction scheme 2 of FIG. 1, the 2,4-bis (methoxymethoxy)bromobenzene (7) is reacted, in the presence of a base such as butyllithium, for example, with a heterocycloalkanone of general formula (2), which is commercially available or prepared according to conventional synthesis methods (W. D. Langley, Org. Synth. I, 122 (1932)), so as to give the benzyl alcohol of general formula (8).

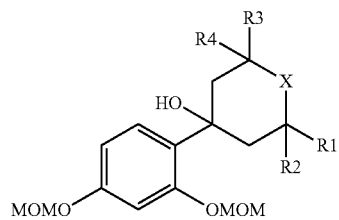
(8)

The benzyl alcohol of general formula (8) is dehydrated to give the compound of general formula (9), in a solvent such as toluene, in the presence of an acid such as camphorsulphonic acid, for example.

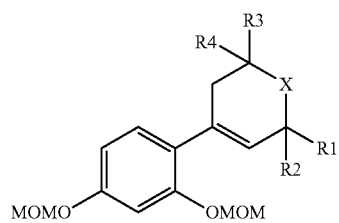
(9)

The compounds of general formula (10) are obtained by hydrogenation of the compounds of general formula (9) in the presence of hydrogen in a solvent such as methanol, for example, and of a palladium-based catalyst such as palladium-on-charcoal, for example.

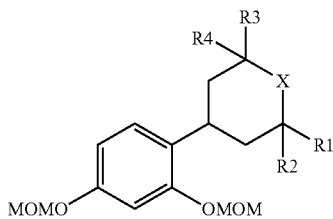
(10)

The compounds of general formula (5) are obtained starting from the compounds of general formula (10) in the presence of hydrochloric acid in methanol, for example.

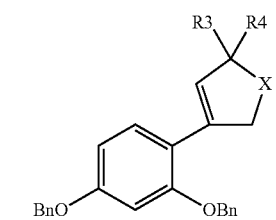
(5)

Scheme 3 of FIG. 1 corresponds to the preparation of the compounds of general formula (I) for which m=1, n=0, X=O, R1=R2=H, and R3, R4 and Y have the same definition as above.

Using reaction scheme 3 of FIG. 1, the 2,4-di-benzyloxy-bromobenzene (1) is reacted, in the presence of butyllithium, for example, with a heterocyclo-alkanone of general formula (11), which is commercially available or prepared according to conventional synthesis methods (W. D. Langley, Org. Synth. I, 122 (1932)), so as to give the compound of general formula (12).

(12)

The compounds of general formula (13) are obtained starting from the compounds of general formula (12) by hydrogenation in a solvent such as methanol for example, in the presence of hydrogen and of a palladium-based catalyst such as palladium-on-charcoal, for example.

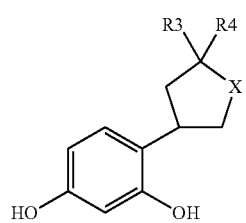
(13)

The compounds of general formula (16):

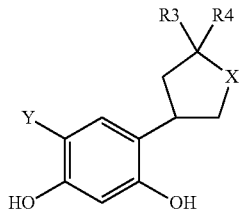

(16)

are obtained by halogenation of the compounds of general formula (13) using a halogenating agent such as N-chlorosuccinimide (Y=Cl) or Selectfluor® (Y=F), for example.

Scheme 4 of FIG. 1 corresponds to the preparation of the compounds of general formula (I) for which m=1, n=0, X=O or S, R1=R2=H, and R3, R4 and Y have the same definition as above.

Using reaction scheme 4 of FIG. 1, the 2,4-bis-(methoxymethoxy)bromobenzene (7) is reacted, in the presence of butyllithium, for example, with a hetero-cycloalkanone of general formula (11), which is commercially available or prepared according to conventional synthesis methods (W. D. Langley, Org. Synth. I, 122 (1932)), so as to give the benzyl alcohol of general formula (14).

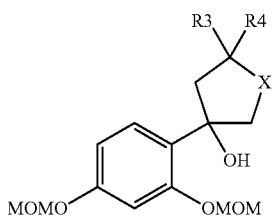

(14)

The benzyl alcohols of general formula (14) are subsequently dehydrated to give the compounds of general formula (15), in a solvent such as methanol, for example, in the presence of an acid such as hydrochloric acid, for example.

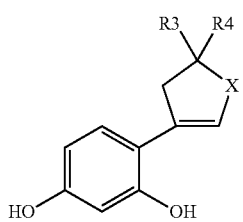

(15)

The compounds of general formula (13) are obtained by hydrogenation of the compounds of general formula (15) in the presence of hydrogen in a solvent such as methanol, for example, and of a palladium-based catalyst such as palladium-on-charcoal, for example.

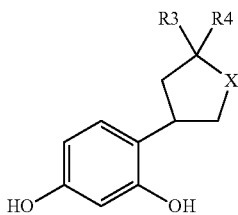

(13)

The invention is therefore directed towards the use of at least one compound of general formula (I) as defined above, as a medicament.

The invention is also directed towards the use, as a medicament, of at least one compound of general formula (I) as defined above, in which said compound has a tyrosinase-inhibiting activity.

The invention is also directed towards the use of at least one compound of general formula (I) as defined above, for the preparation of a pharmaceutical or cosmetic composition in which said compound has a tyrosinase-inhibiting activity.

Advantageously, the compounds of the present invention have an $IC_{50}$ value (dose which inhibits 50% of the enzymatic activity) with respect to tyrosinase of less than or equal to 10 µM, and more particularly less than or equal to 1 µM.

The invention also relates to a compound of general formula (I) for use thereof in the treatment and/or prevention of pigmentary disorders.

In fact, the compounds of general formula (I) according to the invention are particularly suitable for use related to the treatment or prevention of pigmentary disorders such as melasma, chloasma, lentigines, senile lentigo, irregular hyper-pigmentations related to photoageing, freckles, post-inflammatory hyperpigmentations due to an abrasion, a burn, a scar, dermatosis, a contact allergy; naevi, genetically determined hyperpigmentations, hyper-pigmentations of metabolic or drug-related origin, melanomas or any other hyper-pigmentary lesion.

A subject of the present invention is also a pharmaceutical composition for use in particular in the treatment of the abovementioned conditions, and which is characterized in that it comprises, in a pharmaceutically acceptable carrier that is compatible with the method of administration selected for said composition, a compound of general formula (I) in one of its isomer and enantiomer forms, or a salt thereof with a pharmaceutically acceptable base.

The term "pharmaceutically acceptable carrier" is intended to mean a medium that is compatible with the skin, the mucous membranes and the skin appendages.

The composition according to the invention can be administered topically. Preferably, the pharmaceutical composition is packaged in a form suitable for topical application.

When used topically, the pharmaceutical composition according to the invention is more particularly for use in the treatment of the skin and the mucous membranes and may be in liquid, pasty or solid form, and more particularly in the form of ointments, creams, solutions or gels.

The compositions used for topical application have a concentration of compound according to the invention of generally between 0.001% and 10% by weight, preferably between 0.01% and 5% by weight, relative to the total weight of the composition.

The compounds of general formula (I) according to the invention also find a use in the cosmetics field, in particular in protecting against the harmful aspects of the sun, for preventing and/or combating photoinduced or chronological ageing of the skin and skin appendages.

A subject of the invention is therefore also a composition comprising, in a cosmetically acceptable carrier, at least one of the compounds of general formula (I). The term "cosmetically acceptable medium" is intended to mean a medium that is compatible with the skin, the mucous membranes and the skin appendages.

A subject of the invention is also the cosmetic use of a composition comprising at least one compound of general formula (I), for preventing and/or treating the signs of ageing and/or the skin.

A subject of the invention is also the cosmetic use of a composition comprising at least one compound of general formula (I), for body or hair hygiene.

The cosmetic composition according to the invention containing, in a cosmetically acceptable carrier, a compound of general formula (I), or one of its isomer and enantiomer forms or a salt thereof with a cosmetically acceptable base, may be in particular in the form of a cream, a milk, a gel, suspensions of microspheres or nanospheres or lipid or polymeric vesicles, impregnated pads, solutions, sprays, foams, sticks, soaps, washing bases or shampoos.

The concentration of compound of general formula (I) in the cosmetic composition is preferably between 0.001% and 10% by weight, relative to the total weight of the composition.

The pharmaceutical and cosmetic compositions as described above may also contain inert additives, or even pharmacodynamically active additives as regards the pharmaceutical compositions, or combinations of these additives, and in particular:
  wetting agents;
  flavour enhancers;
  preservatives, such as para-hydroxybenzoic acid esters;
  stabilizers;
  moisture regulators;
  pH regulators;
  osmotic pressure modifiers;
  emulsifiers;
  UV-A and UV-B screening agents;
  antioxidants, such as α-tocopherol, butylated hydroxyanisole or butylated hydroxytoluene, superoxide dismutase, ubiquinol; sodium metabisulphite;
  emollients;
  moisturizing agents, such as glycerol, PEG 400, thiamorpholinone and its derivatives, or urea;
  antiseborrheic or antiacne agents, such as S-carboxy-methylcysteine, S-benzylcysteamine, salts thereof or derivatives thereof, or benzoyl peroxide.

Of course, those skilled in the art will take care to select the optional compound(s) to be added to these compositions in such a way that the advantageous properties intrinsically associated with the present invention are not, or not substantially, impaired by the envisaged addition.

Several examples of the preparation of compounds of general formula (I) according to the invention, results for biological activity of these compounds and also various formulations based on such compounds will now be given by way of illustration and without any limiting nature.

EXAMPLE 1

4-(Tetrahydropyran-4-yl)benzene-1,3-diol a) 4-(2,4-Bis(benzyloxy)phenyl)tetrahydropyran-4-ol 2.4 ml of 2.5 M n-butyllithium in hexane are added to a solution of 1.85 g of 2,4-bis(benzyloxy)-1-bromobenzene in 20 ml of tetrahydrofuran, cooled to −70° C. The reaction medium is stirred at −70° C. for 1 hour, and 555 µl of tetrahydro-4H-pyran-4-one are added. The reaction medium is stirred at −70° C. for 1 hour and then left to return to ambient temperature overnight. The reaction medium is poured into 15 ml of a saturated solution of ammonium chloride to which 2 ml of 2M hydrochloric acid have been added, and is then extracted with ethyl acetate. The organic phases are combined, dried over magnesium sulphate and evaporated. The residue is chromatographed on silica gel, elution being carried out with 70/30 heptane/ethyl acetate.

820 mg of 4-(2,4-bis(benzyloxy)phenyl)tetrahydro-pyran-4-ol are obtained in the form of a white solid. Yield=42%.

b) 4-(Tetrahydropyran-4-yl)benzene-1,3-diol

A mixture of 815 mg of 4-(2,4-bis(benzyloxy)-phenyl)tetrahydropyran-4-ol in 10 ml of ethyl acetate, in the presence of 244 mg of palladium-on-charcoal at 10%, is stirred at ambient temperature under a hydrogen pressure of 5 bar for 17 hours. The reaction medium is filtered and then the filtrate is evaporated. The residue (394 mg) is crystallized from ethyl acetate.

275 mg of 4-(tetrahydropyran-4-yl)benzene-1,3-diol are obtained in the form of a white crystalline solid. Yield=68%.

$^1$H NMR (DMSO D6, 400 MHz): 1.54 (m, 4H); 2.92 (m, 1H); 3.39 (m, 2H); 3.90 (m, 2H); 6.14 (dd, J=8.4 & 2.4 Hz, 1H); 6.25 (d, J=2.4 Hz, 1H); 6.82 (d, J=8.4 Hz, 1H); 8.95 (s, 1H); 9.11 (s, 1H).

$^{13}$C NMR (DMSO D6, 100 MHz): 32.6, 33.5, 67.7, 102.3, 106.0, 122.4, 126.7, 155.2, 156.0.

EXAMPLE 2

4-(Tetrahydrothiopyran-4-yl)benzene-1,3-diol a) 1-Bromo-2,4-bis(methoxymethoxy)benzene 42.56 g of potassium carbonate are added to a solution of 20.0 g of 4-bromoresorcinol at 97% in 200 ml of acetone. The reaction medium is stirred at 5° C. for 10 minutes and then 23.4 ml of chloromethyl methyl ether are added dropwise. The reaction medium is stirred at ambient temperature for 3 hours. The solvent is evaporated off and then the residue is taken up with a water-ethyl acetate mixture. The aqueous phase is extracted with ethyl acetate, and the organic phases are combined, washed with a saturated solution of sodium chloride, dried over magnesium sulphate, filtered and evaporated. The residue is chromatographed on silica gel, elution being carried out with 90/10 heptane/ethyl acetate.

27.94 g of 1-bromo-2,4-bis(methoxymethoxy)benzene are obtained in the form of a colourless oil. Yield=99%.

b) 4-(2,4-Bis(methoxymethoxy)phenyl)tetrahydrothio-pyran-4-ol 6.35 ml of tetramethylethylenediamine are added to a solution of 5.54 g of 1-bromo-2,4-bis(methoxy-methoxy)benzene in 80 ml of tetrahydrofuran. The mixture is cooled to −70° C. and 16.8 ml of 2.5M n-butyllithium in hexane are added. The reaction medium is stirred at −70° C. for 1 hour and 2.79 g of tetrahydrothiopyran-4-one in solution in 30 ml of tetrahydrofuran are added. The reaction medium is stirred at −70° C. for 1 hour and then left at ambient temperature overnight. 50 ml of 2M hydrochloric acid are added and the reaction medium is vigorously stirred for 15 minutes and then extracted with ethyl acetate. The organic phases are combined, washed with a saturated solution of sodium chloride, dried over magnesium sulphate and evaporated. The residue is chromatographed on silica gel, elution being carried out with a 75/25 mixture of heptane/ethyl acetate.

2.97 g of 4-(2,4-bis(methoxymethoxy)phenyl)tetra-hydrothiopyran-4-ol are obtained in the form of a yellow oil. Yield=47%.

c) 5-(2,4-Bis(methoxymethoxy)phenyl)-3,6-dihydro-2H-thiopyran 22 mg of camphorsulphonic acid are added to a solution of 2.96 g of 4-(2,4-bis(methoxymethoxy)-phenyl)tetrahydrothiopyran-4-ol in 60 ml of toluene. The mixture is refluxed for 1 hour. The solvent is evaporated off and the residue is chromatographed on silica gel, elution being carried out with 80/20 heptane/ethyl acetate.

1.90 g of 5-(2,4-bis(methoxymethoxy)phenyl)-3,6-dihydro-2H-thiopyran are obtained in the form of a yellowish oil. Yield=68%.

d) 4-(2,4-Bis(methoxymethoxy)phenyl)tetrahydrothiopyran

A mixture of 1.89 g of 4-(2,4-bis(methoxymethoxy)-phenyl)-3,6-dihydro-2H-thiopyran in 20 ml of ethyl acetate in the presence of 1.89 g of palladium-on-charcoal at 10% is stirred at 50° C. under a hydrogen pressure of 80 bar for 8 hours. The reaction medium is filtered through celite and the filtrate is evaporated.

1.48 g of 4-(2,4-bis(methoxymethoxy)phenyl)tetrahydrothiopyran are obtained in the form of an oil. Yield=77%.

e) 4-(Tetrahydrothiopyran-4-yl)benzene-1,3-diol 18 ml of 1M hydrochloric acid are added to a solution of 1.47 g of 4-(2,4-bis(methoxymethoxy)-phenyl)tetrahydrothiopyran in 18 ml of methanol in the presence of 3 ml of ethyl acetate. The mixture is stirred at ambient temperature for 3 hours and heated at 50° C. for 17 hours. 12.0 ml of a saturated solution of sodium hydrogen carbonate are added to the reaction medium, which is vigorously stirred for 20 minutes and then separated by settling out. The aqueous phase is extracted with ethyl acetate. The organic phases are combined, washed with a saturated solution of sodium chloride, dried over magnesium sulphate, filtered and evaporated. The residue is chromatographed on silica gel, elution being carried out with 70/30 heptane/ethyl acetate. The solid obtained is taken up with diethyl ether and heptane, filtered and dried.

The solid obtained is crystallized from diethyl ether, filtered and dried.

30 mg of 4-(tetrahydrothiopyran-4-yl)benzene-1,3-diol are obtained in the form of a white powder. Yield=3%.

$^1$H NMR (DMSO D6, 400 MHz): 1.61 (m, 2H); 1.92 (m, 2H); 2.55 (m, 2H), 2.72 (m, 3H); 6.14 (dd, J=8.4 & 2.4 Hz, 1H); 6.25 (d, J=2.4 Hz, 1H); 6.80 (d, J=8.4 Hz, 1H); 8.95 (s, 1H); 9.10 (s, 1H).

$^{13}$C NMR (DMSO D6, 100 MHz): 28.7, 33.8, 35.6, 102.3, 106.0, 123.5, 126.7, 154.8, 156.0.

EXAMPLE 3 cis-4-(2,6-Dimethyltetrahydropyran-4-yl)-benzene-1,3-diol a) cis-2,6-Dimethyltetrahydropyran-4-one 10 g of 2,6-dimethyl-gamma-pyrone are dissolved in 200 ml of methanol and then 0.8 g of palladium-on-charcoal at 10% is added. The reaction mixture is stirred for 24 hours under 25 atmospheres of hydrogen. The medium is filtered and then the solvent is evaporated off. 8.81 g of cis-2,6-dimethyltetrahydro-pyran-4-one are recovered. Yield=88%.

b) 4-(2,4-Bis(methoxymethoxy)phenyl)-2,6-dimethyltetra-hydropyran-4-ol 3.0 ml of tetramethylethylenediamine are added to a solution of 2.65 g of 1-bromo-2,4-bis(methoxy-methoxy)benzene in 40 ml of tetrahydrofuran. The mixture is cooled to −70° C. and 8.0 ml of 2.5M n-butyl-lithium in hexane are added. The reaction medium is stirred at −70° C. for 1 hour and 1.47 g of cis-2,6-dimethyltetrahydropyran-4-one in solution in 15 ml of tetrahydrofuran are added. The reaction medium is stirred at −70° C. for 1 hour and then left at ambient temperature overnight. 25 ml of 2M hydrochloric acid are added and the reaction medium is stirred vigorously for 15 minutes and then extracted with ethyl acetate. The organic phases are combined, washed with a saturated solution of sodium chloride, dried over magnesium sulphate and evaporated. The residue is chromatographed on silica gel, elution being carried out with 75/25 heptane/ethyl acetate.

562 mg of 4-(2,4-bis(methoxymethoxy)phenyl)-2,6-dimethyltetrahydropyran-4-ol are obtained in the form of a yellow oil. Yield=18%.

c) 4-(2,4-Bis(methoxymethoxy)phenyl)-2,6-dimethyl-3,6-dihydro-2H-pyran 2 mg of camphorsulphonic acid are added to a solution of 247 mg of 4-(2,4-bis(methoxymethoxy)-phenyl)-2,6-dimethyltetrahydropyran-4-ol in 5 ml of toluene. The mixture is refluxed for 2 hours. The solvent is evaporated and the residue is chromatographed on silica gel, elution being carried out with an 80/20 mixture of heptane/ethyl acetate.

132 mg of 4-(2,4-bis(methoxymethoxy)phenyl)-2,6-dimethyl-3,6-dihydro-2H-pyran are obtained in the form of a yellow oil. Yield=57%.

d) cis-4-(2,4-Bis(methoxymethoxy)phenyl)-2,6-dimethyl-tetrahydropyran

A mixture of 132 mg of cis-4-(2,4-bis(methoxymethoxy)phenyl)-2,6-dimethyl-3,6-dihydro-2H-pyran in 10 ml of methanol, in the presence of 28 mg of palladium-on-charcoal at 10%, is stirred at ambient temperature under a hydrogen pressure of 3 bar for 5 hours. The reaction medium is filtered and the filtrate is then evaporated off.

125 mg of cis-4-(2,4-bis(methoxymethoxy)phenyl)-2,6-dimethyltetrahydropyran are obtained in the form of a white powder. Y=94%.

e) cis-4-(2,6-Dimethyltetrahydropyran-4-yl)benzene-1,3-diol 1.9 ml of 1N hydrochloric acid are added to a solution of 120 mg of cis-4-(2,4-bis(methoxymethoxy)-phenyl)-2,6-dimethyltetrahydropyran in 2.5 ml of methanol. The mixture is stirred at ambient temperature overnight and then refluxed for 1 hour. 1.5 ml of a saturated solution of sodium hydrogen carbonate are added and the reaction medium is stirred vigorously for 20 minutes and then separated by settling out. The aqueous phase is extracted with ethyl acetate. The organic phases are combined, washed with a saturated solution of sodium chloride, dried over magnesium sulphate, filtered and evaporated. The residue is chromatographed on silica gel, elution being carried out with 95/5 dichloromethane/methanol. 40 mg of cis-4-(2,6-dimethyltetrahydropyran-4-yl)benzene-1,3-diol are obtained in the form of a white powder. Yield=46%.

$^1$H NMR (DMSO D6, 400 MHz): 1.09 (d, J=6 Hz, 6H); 1.14 (q, J=12.4 Hz, 2H); 1.61 (dd, J=1.6 Hz & 12.3 Hz, 2H); 2.95 (m, 1H); 3.50 (m, 2H); 6.14 (dd, J=8.4 & 2.4 Hz, 1H); 6.25 (d, J=2.4 Hz, 1H); 6.79 (d, J=8.4 Hz, 1H); 8.94 (s, 1H); 9.09 (s, 1H).

$^{13}$C NMR (DMSO D6, 100 MHz): 21.9, 33.4, 72.7, 102.3, 105.9, 122.3, 126.6, 155.1, 155.9.

EXAMPLE 4 trans-4-(2-Methyltetrahydropyran-4-yl)-benzene-1,3-diol a) 2-Methyl-2,3-dihydropyran-4-one 1.7 ml of BF$_3$.Et$_2$O are added to a solution of 2.07 g of Danishefsky's diene (((E)-3-methoxy-1-methyleneallyloxy)trimethylsilane) and 581 mg of acetaldehyde in 25 ml of diethyl ether, cooled to −70° C. The mixture is stirred at −70° C. for 1 hour. 10 ml of a saturated solution of sodium hydrogen carbonate are added and the reaction medium is extracted with diethyl ether. The organic phases are combined, dried over magnesium sulphate, filtered and cold-evaporated.

1.35 g of 2-methyl-2,3-dihydropyran-4-one are obtained in the form of an orange oil. Yield=100%.

b) 2-Methyltetrahydropyran-4-one 1.35 g of 2-methyl-2,3-dihydropyran-4-one in 15 ml of ethyl acetate, in the presence of 270 mg of palladium-on-charcoal at 10%, are stirred under a hydrogen atmosphere at ambient temperature for 3 days. The reaction medium is filtered through filter paper and the filtrate is evaporated. The residue is chromatographed on silica gel, elution being carried out with 60/40 pentane/diethyl ether.

787 mg of 2-methyltetrahydropyran-4-one are obtained in the form of a yellow oil. Yield=57%.

c) 4-(2,4-Bis(benzyloxy)phenyl)-2-methyltetrahydropyran-4-ol 2.7 ml of 2.5M n-butyllithium in hexane are added to a solution of 2.06 g of 2,4-bis(benzyloxy)-1-bromobenzene in 20 ml of tetrahydrofuran, cooled to −70° C. The reaction medium is stirred at −70° C. for 10 minutes and 766 mg of 2-methyltetrahydropyran-4-one in solution in 7 ml of tetrahydrofuran are added. The reaction medium is stirred at −70° C. for 1 hour and is then left to return to ambient temperature for 3 hours. The reaction medium is poured into 20 ml of a saturated solution of ammonium chloride to which 3 ml of 2M hydrochloric acid have been added, and is then extracted with ethyl acetate. The organic phases are combined, dried over magnesium sulphate and evaporated. The residue is chromatographed on silica gel, elution being carried out with 70/30 heptane/ethyl acetate.

838 mg of 4-(2,4-bis(benzyloxy)phenyl)-2-methyl-tetrahydropyran-4-ol are obtained in the form of a yellow oil. Yield=37%.

d) trans-4-(2-Methyltetrahydropyran-4-yl)benzene-1,3-diol 830 mg of 4-(2,4-bis(benzyloxy)phenyl)-2-methyl-tetrahydropyran-4-ol in 12 ml of ethyl acetate, in the presence of 415 mg of palladium-on-charcoal at 10%, are stirred at ambient temperature under a hydrogen pressure of 5 bar for 3 hours. The reaction medium is filtered and then the filtrate is evaporated. The residue (516 mg) is chromatographed on silica gel, elution being carried out with 80/20 heptane/ethyl acetate.

37 mg of trans-4-(2-methyltetrahydropyran-4-yl)-benzene-1,3-diol are obtained in the form of a white powder. Yield=8%.

$^1$H NMR (DMSO D6, 400 MHz): 1.20 (d, J=6 Hz, 3H); 1.48 (m, 1H); 1.58 (m, 2H); 1.79 (m, 1H); 3.16 (m, 1H); 3.56 (m, 1H); 3.67 (m, 1H); 3.94 (m, 1H); 6.14 (dd, J=8.4 & 2.4 Hz, 1H); 6.25 (d, J=2.4 Hz, 1H); 6.79 (d, J=8.4 Hz, 1H); 8.95 (s, 1H); 9.11 (s, 1H).

$^{13}$C NMR (DMSO D6, 100 MHz): 18.3, 27.5, 31.4, 36.4, 60.9, 68.1, 102.4, 105.8, 122.1, 127.1, 155.4, 156.0.

EXAMPLE 5 cis-4-(2-Methyltetrahydropyran-4-yl)benzene-1,3-diol

In the preceding purification, a more polar fraction is isolated: 57 mg of cis-4-(2-methyl-tetrahydropyran-4-yl)benzene-1,3-diol are obtained in the form of a white powder. Yield=13%.

$^1$H NMR (DMSO D6, 400 MHz): 1.10 (d, J=6 Hz, 3H); 1.20 (m, 1H); 1.50 (m, 2H); 1.62 (m, 1H); 2.94 (m, 1H); 3.42 (m, 2H); 3.90 (m, 1H); 6.14 (dd, J=8.4 & 2.4 Hz, 1H); 6.25 (d, J=2.4 Hz, 1H); 6.80 (d, J=8.4 Hz, 1H); 8.95 (s, 1H); 9.10 (s, 1H).

$^{13}$C NMR (DMSO D6, 100 MHz): 21.9, 31.9, 33.5, 40.7, 67.3, 73.1, 102.3, 106.0, 122.4, 126.7, 155.1, 156.0.

EXAMPLE 6 trans-4-(2-Ethyltetrahydropyran-4-yl)-benzene-1,3-diol

In a manner analogous to Example 4, but using propionaldehyde in stage 4a and then reproducing stages 4b, 4c and 4d in an analogous manner, trans-4-(2-ethyl-tetrahydropyran-4-yl)benzene-1,3-diol is obtained.

$^1$H NMR (DMSO D6, 400 MHz): 0.81 (t, J=6 Hz, 3H); 1.20 (m, 1H); 1.45-1.65 (m, 5H); 2.92 (m, 1H); 3.21 (m, 1H); 3.40 (td, J=11.2 & 2.4 Hz, 1H); 3.90 (m, 1H); 6.14 (dd, J=8.4 & 2.4 Hz, 1H); 6.25 (d, J=2.4 Hz, 1H); 6.79 (d, J=8.4 Hz, 1H); 8.95 (s, 1H); 9.11 (s, 1H).

$^{13}$C NMR (DMSO D6, 100 MHz): 9.9, 28.8, 32.2, 33.5, 37.7, 67.5, 78.4, 102.4, 106.0, 122.5, 126.7, 155.1, 156.0.

EXAMPLE 7 cis-4-(2-Ethyltetrahydropyran-4-yl)benzene-1,3-diol

In a manner analogous to Example 5, a more polar fraction is obtained by purifying the product obtained in the synthesis of Example 6; cis-4-(2-ethyl-tetrahydropyran-4-yl)benzene-1,3-diol is obtained.

$^1$H NMR (DMSO D6, 400 MHz): 0.90 (t, J=6 Hz, 3H); 1.50 (m, 1H); 1.61 (m, 3H); 1.81 (m, 2H); 3.22 (m, 1H); 3.69 (m, 3H); 3.67 (m, 1H); 3.94 (m, 1H); 6.14 (dd, J=8.4 & 2.4 Hz, 1H); 6.25 (d, J=2.4 Hz, 1H); 6.79 (d, J=8.4 Hz, 1H); 8.95 (s, 1H); 9.11 (s, 1H).

$^{13}$C NMR (DMSO D6, 100 MHz): 10.3, 24.2, 27.8, 31.4, 34.6, 61.0, 73.8, 102.4, 105.8, 122.2, 127.0, 155.4, 156.0.

EXAMPLE 8 trans-4-(2-Hydroxymethyltetrahydropyran-4-yl)benzene-1,3-diol

In a manner analogous to Example 4, but using benzyloxyacetaldehyde in stage 4a and then reproducing stages 4b, 4c and 4d in an analogous manner, trans-4-(2-hydroxymethyltetrahydropyran-4-yl)benzene-1,3-diol is obtained.

$^1$H NMR (DMSO D6, 400 MHz): 1.20 (m, 1H); 1.55 (m, 2H); 1.65 (m, 1H); 2.92 (m, 1H); 3.40 (m, 4H); 3.95 (m, 1H); 4.56 (m, 1H); 6.14 (dd, J=8.4 & 2.4 Hz, 1H); 6.25 (d, J=2.4 Hz, 1H); 6.79 (d, J=8.4 Hz, 1H); 8.95 (s, 1H); 9.12 (s, 1H).

$^{13}$C NMR (DMSO D6, 100 MHz): 32.2, 33.2, 34.6, 64.8, 37.3, 78.5, 102.4, 106.0, 122.5, 126.7, 155.2, 156.0.

EXAMPLE 9

4-(2,2,6,6-Tetramethyltetrahydropyran-4-yl)-benzene-1,3-diol a) 2,2,6,6-Tetramethyltetrahydropyran-4-one 5 g of commercial phorone are dissolved in 36 ml of a 1M solution of hydrochloric acid and heated at 40° C. for 2 days. The reaction mixture is distilled (63-65° C.) so as to give 3.0 g of a yellowish oil. Yield=53%.

$^1$H NMR (DMSO D6, 400 MHz): 1.25 (m, 4H); 2.3 (m, 12H).

b) 4-(2,2,6,6-Tetramethyltetrahydropyran-4-yl)benzene-1,3-diol

In a manner analogous to Example 4, but using 2,2,6,6-tetramethyltetrahydropyran-4-one in stage 4c and then reproducing stage 4d in an analogous manner, 4-(2,2,6,6-tetramethyltetrahydropyran-4-yl)benzene-1,3-diol is obtained.

$^1$H NMR (DMSO D6, 400 MHz): 1.11 (s, 6H); 1.25 (m, 8H); 1.56 (m, 2H); 3.28 (m, 1H); 6.14 (dd, J=8.4 & 2.4 Hz, 1H); 6.25 (d, J=2.4 Hz, 1H); 6.79 (d, J=8.4 Hz, 1H); 8.95 (s, 1H); 9.09 (s, 1H).

$^{13}$C NMR (DMSO D6, 100 MHz): 25.8, 27.4, 33.7, 43.0, 71.7, 102.3, 106.0, 122.5, 126.5, 155.2, 155.9.

EXAMPLE 10

4-(Tetrahydrofuran-3-yl)benzene-1,3-diol a) Dihydrofuran-3-one

A solution of 16.8 g of chromium VI oxide in 50 ml of water in the presence of 15.6 ml of 95% sulphuric acid is added dropwise to a solution of 4.9 g of 3-hydroxytetrahydrofuran in 450 ml of acetone. The reaction medium is stirred at 0° C. for 40 minutes. 450 ml of water are added and the reaction medium is extracted with diethyl ether. The organic phases are combined, washed with a saturated solution of sodium chloride, dried over magnesium sulphate, filtered and evaporated. The residue is chromatographed on silica gel, elution being carried out with 60/40 pentane/diethyl ether. 1.78 g of dihydrofuran-3-one are obtained in the form of a colourless oil. Yield=28%.

b) 3-(2,4-Bis(benzyloxy)phenyl)-2,5-dihydrofuran 2 ml of 2.5M n-butyllithium in hexane are added to a solution of 4.74 g of 2,4-bis(benzyloxy)-1-bromobenzene in 50 ml of tetrahydrofuran, cooled to −70° C. The reaction medium is stirred at −70° C. for 10 minutes and 1.77 g of dihydrofuran-3-one in solution in 15 ml of tetrahydrofuran are added. The reaction medium is stirred at −70° C. for 1 hour and is then left to return to ambient temperature overnight. The reaction medium is poured into 35 ml of a saturated solution of ammonium chloride to which 6.5 ml of 2M hydrochloric acid have been added, and is then extracted with ethyl acetate. The organic phases are combined, dried over magnesium sulphate and evaporated. The residue is chromatographed on silica gel, elution being carried out with 60/40 heptane/ethyl acetate.

1.57 g of 3-(2,4-bis(benzyloxy)phenyl)-2,5-dihydrofuran are obtained in the form of a yellow oil. Yield=34%.

c) 4-(Tetrahydrofuran-3-yl)benzene-1,3-diol

A mixture of 1.56 g of 3-(2,4-bis(benzyloxy)-phenyl)tetrahydrofuran-3-ol in 25 ml of ethyl acetate, in the presence of 780 mg of palladium-on-charcoal at 10%, is stirred at ambient temperature under a hydrogen pressure of 5 bar for 7 hours. The reaction medium is filtered and then the filtrate is evaporated. The residue is chromatographed on silica gel, elution being carried out with 50/50 heptane/ethyl acetate. The solid obtained is crystallized from dichloromethane/heptane. 285 mg of 4-(tetrahydrofuran-3-yl)benzene-1,3-diol are obtained in the form of a white powder. Yield=36%.

$^1$H NMR (DMSO D6, 400 MHz): 1.85 (m, 1H); 2.10 (m, 1H); 3.42 (m, 2H); 3.73 (q, J=8.4 Hz, 1H); 3.85 (m, 1H); 3.92 (m, 1H); 6.14 (dd, J=8.4 & 2.4 Hz, 1H); 6.26 (d, J=2.4 Hz, 1H); 6.87 (d, J=8.4 Hz, 1H); 9.02 (s, 1H); 9.21 (s, 1H).

$^{13}$C NMR (DMSO D6, 100 MHz): 32.0, 37.5, 67.2, 72.5, 102.3, 106.0, 118.3, 127.3, 155.8, 156.4.

EXAMPLE 11

4-(Tetrahydrothiophen-3-yl)benzene-1,3-diol a) 3-(2,4-Bis(methoxymethoxy)phenyl)tetrahydrothiophen-3-ol 23.0 ml of 2.5M n-butyllithium in hexane are added to a solution of 13.10 g of 1-bromo-2,4-bis-(methoxymethoxy)benzene in 200 ml of tetrahydrofuran, cooled to −70° C. The reaction medium is stirred at −70° C. for 20 minutes and 4.90 ml of tetrahydrothiophen-3-one are added. The reaction medium is stirred at −70° C. for 1 hour and is then left to return to ambient temperature overnight. The reaction medium is poured into 150 ml of a saturated solution of ammonium chloride to which 30 ml of 2M hydrochloric acid have been added, and is then extracted with ethyl acetate. The organic phases are combined, dried over magnesium sulphate and evaporated. The residue is chromatographed on silica gel, elution being carried out with 85/15 heptane/ethyl acetate.

4.10 g of 3-(2,4-bis(methoxymethoxy)phenyl)tetra-hydrothiophen-3-ol are obtained in the form of an orange oil. Yield=29%.

b) 4-(4,5-Dihydrothiophen-3-yl)benzene-1,3-diol 50 ml of 1N hydrochloric acid are added to a solution of 4.10 g of 3-(2,4-bis(methoxymethoxy)-phenyl)tetrahydrothiophen-3-ol in 50 ml of methanol in the presence of 8 ml of ethyl acetate. The mixture is heated at 50° C. for 4 hours. 40 ml of a saturated solution of sodium hydrogen carbonate are added and the reaction medium is stirred vigorously for 20 minutes and then separated by settling out. The aqueous phase is extracted with ethyl acetate. The organic phases are combined, washed with a saturated solution of sodium chloride, dried over magnesium sulphate, filtered and evaporated. The residue is chromatographed on silica gel, elution being carried out with 80/20 heptane/ethyl acetate.

400 mg of 4-(4,5-dihydrothiophen-3-yl)benzene-1,3-diol are obtained in the form of a yellow oil. Yield=15%.

c) 4-(Tetrahydrothiophen-3-yl)benzene-1,3-diol

A mixture of 400 mg of 4-(4,5-dihydrothiophen-3-yl)benzene-1,3-diol in 10 ml of ethyl acetate, in the presence of 400 mg of palladium-on-charcoal at 10%, is stirred at ambient temperature under a hydrogen pressure of 6 bar for 4 days. The reaction medium is filtered and then the filtrate is evaporated. The residue is chromatographed on silica gel, elution being carried out with 80/20 heptane/ethyl acetate. The solid obtained is crystallized from dichloromethane/heptane.

232 mg of 4-(tetrahydrothiophen-3-yl)benzene-1,3-diol are obtained in the form of a cream solid. Yield=57%.

$^1$H NMR (DMSO D6, 400 MHz): 1.94 (m, 1H); 2.16 (m, 1H); 2.67 (t, J=9.8 Hz, 1H); 2.81 (m, 2H); 2.99 (m, 1H); 3.37 (m, 1H); 6.14 (dd, J=8.4 & 2.4 Hz, 1H); 6.27 (d, J=2.4 Hz, 1H); 6.95 (d, J=8.4 Hz, 1H); 9.05 (s, 1H); 9.27 (s, 1H).

$^{13}$C NMR (DMSO D6, 100 MHz): 29.9, 35.5, 35.6, 42.5, 102.5, 106.4, 118.0, 127.0, 155.7, 156.6.

EXAMPLE 12

4-(6-Oxaspiro[4.5]dec-9-yl)benzene-1,3-diol a) 6-Oxaspiro[4.5]decan-9-one

At ambient temperature, 5 g of (E)-3-[(tert-butyl-dimethylsilanyloxy)buta-1,3-dienyl]dimethylamine are added to a solution of 3.9 g of cyclopentanone in 11 ml of 2-butanol. The reaction mixture is stirred for 18 h at ambient temperature. The solvent is evaporated off and then the residue is taken up in 100 ml of diethyl ether. The mixture is cooled to −78° C. and then 1.9 ml of acetyl chloride are added slowly. The mixture is stirred for 10 min at −78° C. and then the reaction is stopped by adding 100 ml of a saturated solution of ammonium chloride. The resulting mixture is extracted with 200 ml of diethyl ether, and the organic phases are combined, and then dried over anhydrous sodium sulphate. The residue is chromatographed on silica gel (8/2 heptane/ethyl acetate). The residue is dissolved in 50 ml of methanol, and then 200 mg of palladium-on-charcoal at 10% are added. The reaction mixture is stirred for 2 hours under a hydrogen atmosphere. The reaction mixture is filtered and then the methanol is evaporated off. 600 mg of 6-oxaspiro[4.5]decan-9-one are obtained. Yield=18%.

b) 4-(6-Oxaspiro[4.5]dec-9-yl)benzene-1,3-diol

In a manner analogous to Example 1, but using 6-oxa-spiro[4.5]decan-9-one in stage 1a and then reproducing stage 1b in an analogous manner, 4-(6-oxaspiro[4.5]dec-9-yl)benzene-1,3-diol is obtained.

$^1$H NMR (DMSO D6, 400 MHz): 1.49 (m, 10H); 1.98 (m, 2H); 2.45 (m, 1H); 3.01 (m, 1H); 3.56 (m, 1H); 3.67 (m, 1H); 6.14 (dd, J=8.4 & 2.4 Hz, 1H); 6.25 (d, J=2.4 Hz, 1H); 6.81 (d, J=8.4 Hz, 1H); 8.94 (s, 1H); 9.08 (s, 1H).

$^{13}$C NMR (DMSO D6, 100 MHz): 23.0, 24.1, 30.7, 31.8, 32.3, 41.2, 41.8, 61.9, 83.3, 102.4, 106.0, 122.6, 126.5, 155.2, 156.0.

EXAMPLE 13

4-Chloro-6-(tetrahydropyran-4-yl)benzene-1,3-diol 2.4 g of N-chlorosuccinimide are added to a solution of 2 g of 4-(tetrahydropyran-4-yl)benzene-1,3-diol (Example 1) in 30 ml of dichloromethane at 0° C. The reaction mixture is stirred at ambient temperature for 16 hours. The reaction mixture is extracted with dichloromethane and then washed with water. The organic phases are combined and then dried over sodium sulphate. The residue is chromatographed on silica gel (75/25 heptane/ethyl acetate). 400 mg of 4-chloro-6-(tetrahydropyran-4-yl)benzene-1,3-diol are obtained. Yield=17%.

$^1$H NMR (DMSO D6, 400 MHz): 1.58 (m, 4H), 2.91 (m, 1H), 3.39 (m, 2H), 3.88 (m, 2H), 6.49 (s, 1H), 6.91 (s, 1H), 9.44 (s, 1H), 9.70 (s, 1H).

$^{13}$C NMR (DMSO D6, 100 MHz): 32.3; 33.6; 67.6; 103.6; 109.3; 124.2; 126.9; 151.2; 154.0.

EXAMPLE 14

4-Fluoro-6-(tetrahydropyran-4-yl)benzene-1,3-diol 3.65 g of N-fluoro-N'-(chloromethyl)triethylenediamine bis(tetrafluoroborate) are added to a solution of 2 g of 4-(tetrahydropyran-4-yl)benzene-1,3-diol (Example 1) in 20 ml of acetonitrile at 0° C. The reaction mixture is stirred for 16 hours at ambient temperature. The reaction mixture is extracted with ethyl acetate, and the organic phases are washed and then dried over sodium sulphate. The residue is chromatographed on silica gel (9/1 heptane/ethyl acetate). 200 mg of 4-fluoro-6-(tetrahydropyran-4-yl)benzene-1,3-diol are obtained. Yield=10%.

$^1$H NMR (DMSO D6, 400 MHz): 1.62 (m, 4H); 2.98 (m, 41H); 3.44 (m, 2H); 3.94 (m, 2H); 6.49 (s, 1H); 6.83 (s, 1H); 9.16 (s, 1H); 9.45 (s, 1H).

$^{13}$C NMR (DMSO D6, 100 MHz): 32.3, 33.4, 67.6, 104.4, 113.3 ($J_{CF}$=19 Hz), 122.3, 142.4 ($J_{CF}$=13 Hz), 144.6 ($J_{CF}$=229 Hz), 150.4.

EXAMPLE 15

4-(2,2-Diethyltetrahydropyran-4-yl)benzene-1,3-diol

In a manner analogous to Example 12a, but using diethyl ketone and then reproducing stage 12b in an analogous manner, 4-(2,2-diethyltetrahydropyran-4-yl)-benzene-1,3-diol is obtained.

$^1$H NMR (DMSO D6, 400 MHz): 0.82 (t, J=6.7 Hz, 6H); 1.22-1.64 (m, 8H); 1.85 (m, 1H); 3.18 (m, 1H); 3.66 (m, 2H); 6.20 (dd, J=8.4 & 2.4 Hz, 1H); 6.31 (d, J=2.4 Hz, 1H); 6.88 (d, J=8.4, Hz, 1H); 9.00 (s, 1H); 9.14 (s, 1H).

$^{13}$C NMR (DMSO D6, 100 MHz): 8.8, 22.6, 28.8, 32.2, 32.4, 39.5, 60.9, 75.0, 102.4, 106.0, 122.7, 126.6, 155.2, 156.0.

EXAMPLE 16

4-(tetrahydropyran-3-yl)benzene-1,3-diol

In a manner analogous to Example 1, but using dihydropyran-3-one, 4-(tetrahydropyran-3-yl)benzene-1,3-diol is obtained.

$^1$H NMR (DMSO D6, 400 MHz): 1.54-1.77 (m, 6H); 2.95 (m, 1H); 3.12 (t, J=10.6 Hz, 1H); 3.30 (m, 1H); 3.73 (m, 1H), 3.80 (m, 1H), 6.14 (dd, J=8.4 & 2.4 Hz, 1H); 6.26 (d, J=2.4 Hz, 1H); 6.84 (d, J=8.4, Hz, 1H); 9.00 (s, 1H); 9.18 (s, 1H).
$^{13}$C NMR (DMSO D6, 100 MHz): 26.2, 28.8, 34.9, 67.2, 72.1, 102.3, 106.0, 119.0, 127.3, 155.6, 156.3.

EXAMPLE 17

Tyrosinase Activity Inhibition Assay

The activity of the inhibitors is measured using a lysate of B16F1 cells (murine melanoma line). In the presence of the L-tyrosine substrate, the tyrosinase present in these cells catalyses the hydroxylation of L-tyrosine to give L-DOPA and then the oxidation of the L-DOPA to give dopaquinone. In the presence of MBTH (3-methyl-2-benzothiazolinone hydrazone), the dopaquinone is trapped so as to form a pink complex which absorbs at 520 nm.

The B16F1 cells are cultured in DMEM medium+10% foetal calf serum+$10^{-9}$M α-MSH for 4 days at 37° C. under 7% $CO_2$. They are treated with trypsin, washed in PBS, counted and pelleted. The pellet is taken up at $10^7$ cells/ml in lysis buffer (10 mM sodium phosphate, pH 6.8-1% Igepal) and the suspension is treated with ultrasound for 10 seconds. After centrifugation for 30 minutes at 4000 rpm, the supernatant obtained constitutes the cell lysate used as tyrosinase source in the enzymatic assay.

The assays are carried out in duplicate in 384-well plates in a total volume of 50 μl. Each well contains:
  40 μl of solution containing 1.25 mM L-tyrosine, 6.25 μM L-DOPA (cofactor) and 3.75 mM MBTH in buffer B (62.25 mM sodium phosphate, pH 6.8-2.5% dimethylformamide),
  5 μl of inhibitor diluted in DMSO,
  5 μl of cell lysate diluted to ½ in 50 mM Tris HCl buffer, pH 7.5.

The plate is incubated at 37° C. and a spectro-photometric reading is carried out at 520 nm after 6 hours of incubation. In order to avoid any possible absorption of the products, the system uses corrected absorbance (absorbance at time 6 h—absorbance at time zero).

The inhibitors are assayed in terms of dose-response so as to calculate an $IC_{50}$ (dose which inhibits 50% of the enzymatic activity).

Several internal controls are added to each experiment:
  control for 100% activity: the 5 μl of inhibitor are replaced with 5 μl of DMSO,
  control for 50% activity: the 5 μl of inhibitor are replaced with 5 μl of phenylthiourea at 300 μM in DMSO,
  control for 0% activity: the L-tyrosine substrate is replaced with buffer B.

The results obtained for the compounds of the invention are shown in Table A:

TABLE A

| Name | Structure | Tyrosine hydroxylase/Dopa oxidase $IC_{50}$ (μM) |
| --- | --- | --- |
| 4-butylresorcinol (Rucinol) | | 3 |
| Compound 1 | 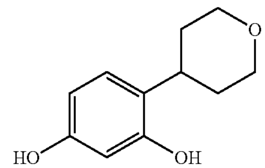 [SMILES: Oc1ccc(C2CCOCC2)c(O)c1] | 0.1 |
| Compound 2 | 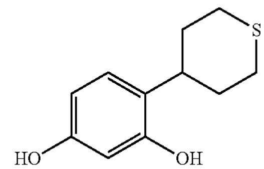 [SMILES: Oc1ccc(C2CCOCC2)c(O)c1] | 0.4 |

EXAMPLE 18

Melanogenesis Inhibition Assay

The inhibition of melanogenesis is measured in MNT1 human melanoma cells according to a protocol adapted from Reigner et al., Cell Mol Biol (1999) 45: 969-980. The assay is based on the concomitant incorporation of 2 radiolabelled tracers: $^{14}$C-thiouracil is incorporated into the neosynthesized melanin and reflects melanogenesis, whereas $^3$H-leucine is incorporated into the proteins and reflects cell viability and, consequently, the toxicity of the compounds tested.

The MNT1 cells are seeded into 96-well plates in the presence of the test compounds and of the radio-isotopes. After incubation for 24 h at 37° C., the cells are washed and the amount of the 2 radioisotopes is measured. The test compounds are evaluated in terms of dose-response so as to calculate an $IC_{50}$ for inhibition of melanogenesis on the basis of the $^{14}$C incorporation which is standardized through the $^3$H incorporation. An $IC_{50}$ for cell toxicity is also calculated on the basis of the $^3$H incorporation.

This assay therefore makes it possible to distinguish the products that specifically inhibit melanogenesis from those which are cytotoxic to melanocytes.

| Name | Formula | $IC_{50}$ melanogenesis | $IC_{50}$ toxicity |
| --- | --- | --- | --- |
| 4-butylresorcinol (Rucinol) | | 15 μM | 55 μM |
| Compound 1 | | 1 μM | >999 μM |

EXAMPLE 19

Formulations

This example illustrates various formulations based on the compounds according to the invention.

| TOPICALLY | |
|---|---|
| (a) Ointment | |
| Compound 1 | 0.020 g |
| Isopropyl myristate | 81.700 g |
| Fluid liquid petroleum jelly | 9.100 g |
| Silica (Aerosil 200) | 9.180 g |
| (b) Ointment | |
| Compound 6 | 0.300 g |
| White petroleum jelly, pharmaceutical grade | qs 100 g |
| (c) Nonionic water-in-oil cream | |
| Compound 1 | 0.100 g |
| Mixture of emulsive lanolin alcohols, of waxes and of oils (anhydrous eucerin) | 39.900 g |
| Methyl para-hydroxybenzoate | 0.075 g |
| Propyl para-hydroxybenzoate | 0.075 g |
| Sterile demineralized water | qs 100 g |
| (d) Lotion | |
| Compound 6 | 0.100 g |
| Polyethylene glycol (PEG 400) | 69.900 g |
| 95% ethanol | 30.000 g |
| (e) Hydrophobic ointment | |
| Compound 2 | 0.300 g |
| Isopropyl myristate | 36.400 g |
| Silicone oil (Rhodorsil 47 V 300) | 36.400 g |
| Beeswax | 13.600 g |
| Silicone oil (Abil 300 000 cst) | qs 100 g |
| (f) Nonionic oil-in-water cream | |
| Compound 4 | 1.000 g |
| Cetyl alcohol | 4.000 g |
| Glyceryl monostearate | 2.500 g |
| PEG 50 stearate | 2.500 g |
| Shea butter | 9.200 g |
| Propylene glycol | 2.000 g |
| Methyl para-hydroxybenzoate | 0.075 g |
| Propyl para-hydroxybenzoate | 0.075 g |
| Sterile demineralized water | qs 100 g |

The invention claimed is:

1. A compound of general formula (I) below:

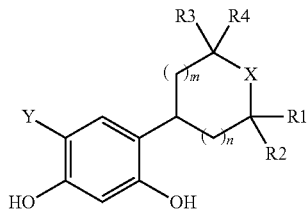

(I)

in which:
R1, R2, R3 and R4, which may be identical or different, represent:
a hydrogen,
a $C_1$-$C_4$ alkyl radical,
a hydroxymethyl, a hydroxyethyl,
a ($C_1$-$C_4$ alkoxy)carbonyl,
a $C_1$-$C_4$ alkoxy,
a hydroxyl,
or
R1 and R2 are linked to one another and form a carbon ring containing 5 or 6 carbon atoms, with the carbon atom to which they are attached, and R3 and R4, which may be identical or different, represent:
a hydrogen,
a $C_1$-$C_4$ alkyl radical,
or
R1 and R4 are linked to one another and form a —($CH_2$)$_2$— or —($CH_2$)$_3$— chain and R2 and R3, which may be identical or different, represent:
a hydrogen,
a $C_1$-$C_4$ alkyl radical,
X represents an oxygen atom or a sulphur atom,
Y represents a hydrogen, a chlorine atom or a fluorine atom,
m can have the value 1 or 2 and n can have the value 0 or 1, and when n=0, then m=1 or 2, and when n=1, then m=1,
and also the salts of the compounds of general formula (I), and the isomer and enantiomer forms thereof.

2. The compound according to claim 1, wherein the compound is in the form of a salt formed with a base selected from the group consisting of an organic base and an inorganic base.

3. The compound according claim 1 wherein:
R1 represents a hydrogen, a $C_1$-$C_4$ alkyl radical or a hydroxymethyl radical,
R2 represents a hydrogen,
R3 represents a hydrogen,
R4 represents a hydrogen,
X represents an oxygen atom,
Y represents a hydrogen or a fluorine atom,
m=1 and n=1,
and also salts of these compounds, and isomer and enantiomer forms thereof.

4. The compound according to claim 1, wherein the compound is selected from the group consisting of:
1: 4-(tetrahydropyran-4-yl)benzene-1,3-diol;
2: 4-(tetrahydrothiopyran-4-yl)benzene-1,3-diol;
3: 4-(cis-2,6-dimethyltetrahydropyran-4-yl)benzene-1,3-diol;
4: trans-4-(2-methyltetrahydropyran-4-yl)benzene-1,3-diol;
5: cis-4-(2-methyltetrahydropyran-4-yl)benzene-1,3-diol;
6: trans-4-(2-ethyltetrahydropyran-4-yl)benzene-1,3-diol;
7: cis-4-(2-ethyltetrahydropyran-4-yl)benzene-1,3-diol;
8: trans-4-(2-hydroxymethyltetrahydropyran-4-yl)benzene-1,3-diol;
9: 4-(2,2,6,6-tetramethyltetrahydropyran-4-yl)benzene-1,3-diol;
10: 4-(tetrahydrofuran-3-yl)benzene-1,3-diol;
11: 4-(tetrahydrothiophen-3-yl)benzene-1,3-diol;
12: 4-(6-oxaspiro[4.5]dec-9-yl)benzene-1,3-diol;
13: 4-chloro-6-(tetrahydropyran-4-yl)benzene-1,3-diol;
14: 4-fluoro-6-(tetrahydropyran-4-yl)benzene-1,3-diol;
15: 4-(2,2-diethyltetrahydropyran-4-yl)benzene-1,3-diol;
16: 4-(tetrahydropyran-3-yl)benzene-1,3-diol;
17: trans-4-(5-hydroxymethyltetrahydrofuran-3-yl)benzene-1,3-diol,
18: cis-4-(5-hydroxymethyltetrahydrofuran-3-yl)benzene-1,3-diol;
19: trans-4-fluoro-6-(5-hydroxymethyltetrahydrofuran-3-yl)benzene-1,3-diol;
20: cis-4-fluoro-6-(5-hydroxymethyltetrahydrofuran-3-yl)benzene-1,3-diol;

21: trans-4-fluoro-6-(2-hydroxymethyltetrahydropyran-4-yl)benzene-1,3-diol;
22: cis-4-fluoro-6-(2-hydroxymethyltetrahydropyran-4-yl)benzene-1,3-diol;
23: cis-4-(8-oxabicyclo[3.2.1]oct-3-yl)benzene-1,3-diol;
24: trans-4-(8-oxabicyclo[3.2.1]oct-3-yl)benzene-1,3-diol; and
25: 4-fluoro-6-(tetrahydrothiopyran-4-yl)benzene-1,3-diol.

5. A medicament comprising an effective amount of at least one compound according to claim 1.

6. The medicament according to claim 5, wherein the at least one compound exhibits a tyrosinase-inhibiting activity.

7. The medicament according to claim 5, wherein the effective amount of the at least one compound is effective to treat a pigmentary disorder selected from the group consisting of melasma, chloasma, lentigines, senile lentigo, irregular hyperpigmentation related to photoageing, freckles, a post-inflammatory hyperpigmentation due to an abrasion, a burn, a scar, dermatosis, a contact allergy, and naevi.

* * * * *